United States Patent
de Graaf et al.

(10) Patent No.: US 6,602,665 B2
(45) Date of Patent: Aug. 5, 2003

(54) REFERENCED AMPLIFICATION OF SMALL QUANTITIES OF RNA

(75) Inventors: David de Graaf, Cambridge, MA (US); Eric S. Lander, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/822,789

(22) Filed: Mar. 30, 2001

(65) Prior Publication Data

US 2002/0172947 A1 Nov. 21, 2002

Related U.S. Application Data

(60) Provisional application No. 60/193,708, filed on Mar. 31, 2000.

(51) Int. Cl.$^7$ .............. C12Q 1/68; C12P 19/34; C07H 21/02; C07H 21/04
(52) U.S. Cl. .......... 435/6; 435/91.1; 435/91.2; 536/23.1; 536/24.3
(58) Field of Search .............. 435/6, 91.1, 91.2; 536/23.1, 24.3

(56) References Cited

U.S. PATENT DOCUMENTS 6,033,584 A   3/2000   Ngo et al. ............... 216/67

FOREIGN PATENT DOCUMENTS

| WO | WO 99/42618 | 8/1999 |
|---|---|---|
| WO | WO 00/43543 | 7/2000 |
| WO | WO 00/46401 | 8/2000 |

OTHER PUBLICATIONS

An, H. X., et al., "ERBB2 Gene Amplification Detected by Fluorescent Differential Polymerase Chain Reaction in Paraffin–Embedded Breast Carcinoma Tissues," *International J. of Cancer*, 64 (5) : 291–297, (1995).

Jennings, B.A., et al., "A differential PCR assay for the detection of c–erbB 2 amplification used in a prospective study of breast cancer," *J. Clin Pathol: Mol. Pathology*, 50 (5) : 254–256, (1997).

Liu, E.T., et al., "Differential polymerase chain reaction in the analysis of gene dosage," *Semin. Cancer Biol.*, 4 (1) : 47–58, (1993).

Robbins, M., and McKinney, M., "Transcriptional regulation of neuromodulin (GAP–43) in mouse neuroblastoma clone N1E–115 as evaluated by the RT/PCR method," *Molecular Brain Research*, 13: 83–92, (1992).

Rochlitz, C.F., "PCR–determined expression of the MDR1 gene in chronic lymphocytic leukemia," *Annals of Hematology*, 65 (6) : 241–246, (1992).

Roetger, A., et al., "Competitive–Differential Polymerase Chain Reaction for Gene Dosage Estimation opf erbB–1 (egfr), erbB–2, and erbB–3 Oncogenes" *DNA and Cell Biology*, 16 (4) : 443–448, (1997).

*Primary Examiner*—Kenneth R. Horlick
*Assistant Examiner*—Teresa Strzelecka
(74) *Attorney, Agent, or Firm*—Hamilton, Brook, Smith & Reynolds, P.C.

(57) ABSTRACT

Methods for determining the amount of an RNA transcript in a test sample are disclosed, utilizing a reference sample comprising a known amount of a reference nucleic acid, labeled with a first strand 3' cDNA primer and a first strand 5' cDNA primer comprising a reference specificity determining box; and a test sample comprising an amount of test RNA containing an RNA transcript of interest, the test RNA being labeled with the first strand 3' cDNA primer and a first strand 5' cDNA primer comprising a test specificity determining box. The reference sample and the test sample are mixed and subjected to polymerase chain reaction amplification conditions, followed by division of the amplified, mixed sample and continued amplification of the divided sample to produce nucleic acids containing amplified reference nucleic acid or amplified cDNA of the test RNA, from which cRNA can be generated by in vitro transcription. The amount of the test RNA, or of the RNA transcript of interest, in the sample correlates with a ratio of the amount of amplified cDNA of the test RNA (or of the RNA transcript of interest), over the amount of the amplified reference nucleic acid, multiplied by the known amount of the reference nucleic acid in the reference sample.

21 Claims, 7 Drawing Sheets

SEQUENCE LISTING

<160> NUMBER OF SEQ ID NOS: 7

<210> SEQ ID NO 1
<211> LENGTH: 48
<212> TYPE: DNA
<213> ORGANISM: Artificial Sequence
<220> FEATURE:
<221> NAME/KEY: misc_feature
<222> LOCATION: 48
<223> OTHER INFORMATION: n = A,T,C or G
<221> NAME/KEY: misc_feature
<222> LOCATION: 47
<223> OTHER INFORMATION: v = A, C, G, not T or U
<221> NAME/KEY: misc_feature
<222> LOCATION: 48
<223> OTHER INFORMATION: n = A,T,C or G
<223> OTHER INFORMATION: oligonucleotide
<221> NAME/KEY: misc_feature
<222> LOCATION: 48

```
<223> OTHER INFORMATION: n = A,T,C or G

<400> SEQUENCE: 1
tcactatagg gaggcggatc gcttttttttt ttttttttttt tttttttvn          48

<210> SEQ ID NO 2
<211> LENGTH: 48
<212> TYPE: DNA
<213> ORGANISM: Artificial Sequence
<220> FEATURE:
<221> NAME/KEY: misc_feature
<222> LOCATION: 48
<223> OTHER INFORMATION: n = A,T,C or G
<221> NAME/KEY: misc_feature
<222> LOCATION: 47
<223> OTHER INFORMATION: v = A, G, C not T or U
<221> NAME/KEY: misc_feature
<222> LOCATION: 48
<223> OTHER INFORMATION: n = A,T,C or G
<223> OTHER INFORMATION: oligonucleotide
<221> NAME/KEY: misc_feature
<222> LOCATION: 48
<223> OTHER INFORMATION: n = A,T,C or G

<400> SEQUENCE: 2
ctcactatag ggaggcggca gcttttttttt ttttttttttt tttttttvn          48

<210> SEQ ID NO 3
<211> LENGTH: 23
<212> TYPE: DNA
<213> ORGANISM: Artificial Sequence
<220> FEATURE:
<223> OTHER INFORMATION: oligonucleotide

<400> SEQUENCE: 3
aagcagtggt aacgcagagt ggg                                       23

<210> SEQ ID NO 4
<211> LENGTH: 21
<212> TYPE: DNA
<213> ORGANISM: Artificial Sequence
<220> FEATURE:
<223> OTHER INFORMATION: oligonucleotide

<400> SEQUENCE: 4
cgactcacta tagggaggcg g                                         21

<210> SEQ ID NO 5
<211> LENGTH: 23
<212> TYPE: DNA
<213> ORGANISM: Artificial Sequence
<220> FEATURE:
<223> OTHER INFORMATION: oligonucleotide

<400> SEQUENCE: 5
aagcagtggt aacaacgcac act                                       23

<210> SEQ ID NO 6
<211> LENGTH: 44
<212> TYPE: DNA
<213> ORGANISM: Artificial Sequence
<220> FEATURE:
<223> OTHER INFORMATION: oligonucleotide

<400> SEQUENCE: 6
ggccagtgaa ttgtaatacg actcactata gggaggcgga tcgt                44
```

-continued

```
<210> SEQ ID NO 7
<211> LENGTH: 45
<212> TYPE: DNA
<213> ORGANISM: Artificial Sequence
<220> FEATURE:
<223> OTHER INFORMATION: oligonucleotide

<400> SEQUENCE: 7
ggccagtgaa ttgtaatacg actcactata gggaggcggc agctt          45
```

REFERENCED AMPLIFICATION OF SMALL QUANTITIES OF RNA

RELATED APPLICATION

This application claims the benefit of U.S. Provisional Application No. 60/193,708, filed on Mar. 31, 2000.

The entire teachings of the above application are incorporated herein by reference.

BACKGROUND OF THE INVENTION

Most biological processes involve large-scale changes in gene expression levels and/or patterns. The advent of microarray technology has made it possible to study these changes in expression in order to identify new complex phenotypic markers or to identify genes involved in particular cellular processes.

The application of microarray technologies is limited by the need for large amounts of RNA; RNA equivalent to the amount present in hundreds of thousands, or even millions, of cells is needed for robust analysis. The requirement of large amounts of RNA precludes the use of microarray technology for the analysis of biological events involving fewer than hundreds of thousands of cells. Thus, gene expression changes in clonal events, such as tumor development and metastasis, as well as multiple small-scale gene expression changes (e.g., as in a heterogeneous tumor), cannot be analyzed. Similarly, processes involving the maturation of a few or single cells, such as the differentiation of stem and germ cells, are out of the grasp of microarray technology.

To overcome problems associated with small amounts of RNA, amplification of RNA samples is frequently performed. Amplification of small amounts of RNA invariably involves a reverse transcription step, followed by either a linear amplification such as the antisense RNA amplification protocol (see, e.g., van Gelder, R. N. et al., *PNAS USA* 87(5):1663–7 (1990); Everwine, J., *Biotechniques* 20(4):584–91 (1996) by an exponential amplification using a polymerase chain reaction (PCR)-mediated amplification (rt-PCR). Both linear and exponential amplification approaches have been used to amplify RNA for microarray analysis (Kacharmina, J. E. et al., *Methods Enzymol.* 303(-HD):3–18 (1999); Spirin, K. S. et al., *Invest. Ophthalmol. Vis. Sci.* 40(13):3108–15 (1999)). Accurate quantification of rt-PCR-amplified gene pools is problematic because of differences in relative amplification efficiencies between RNA transcripts, attributable to many factors (e.g., length of the transcript, secondary structure constrictions and GC content), which can lead to distortion of relative amounts of RNA transcripts in a sample.

SUMMARY OF THE INVENTION

The present invention is drawn to methods for determining the amount of RNA transcripts in a test sample. The methods utilize a reference sample comprising a known amount of a reference nucleic acid; the reference nucleic acid is labeled with a first strand 3' cDNA primer and a first strand 5' cDNA primer comprising a reference specificity determining box. A test sample comprising an amount of test RNA (e.g., containing a particular RNA transcript of interest) is similarly labeled with the same first strand 3' cDNA primer and with a first strand 5' cDNA primer comprising a test specificity determining box. In a preferred embodiment, the 5' cDNA primers contain a partial RNA polymerase promoter sequence (e.g., a partial T7 RNA polymerase promoter sequence), a polyT sequence, and a specificity determining box (either reference or test) between the partial RNA polymerase promoter sequence and the polyT sequence.

The reference sample and the test sample are admixed and subjected to polymerase chain reaction amplification conditions, followed by division of the amplified, mixed sample and continued amplification (such as by PCR or linear extension) of the divided sample using continued amplification primers that specifically bind to either the reference specificity determining box or the test specificity determining box. The resultant nucleic acids contain amplified reference nucleic acid or amplified cDNA of the test RNA, from which cRNA can be made by in vitro transcription. The amount of the test RNA, or of a particular RNA transcript of interest in the sample, can be correlated with a ratio of the amount of amplified cDNA of the test RNA (or RNA transcript of interest in the amplified cDNA of the test RNA) over the amount of the amplified reference nucleic acid, multiplied by the known amount of the reference nucleic acid in the reference sample.

The methods of the invention can be used to facilitate accurate assessment of RNA transcripts in small samples. The methods are simple and less costly than antisense-RNA based methodologies, and provide an added measure of confidence in identifying the presence or absence of gene expression in small samples. Furthermore, the methods allow the use of microarray-based analysis for small RNA samples.

BRIEF DESCRIPTION OF THE DRAWINGS

FIG. 1A, comparison of two samples of unamplified cRNA (0 amplification cycles); FIG. 1B, comparison of a 100 ng sample of cDNA after 20 amplification cycles with the average amount of cDNA in unamplified samples; FIG. 1C, comparison of a 10 ng samples of cDNA after 25 amplification cycles with the average amount of cDNA in unamplified samples; FIG. 1D, comparison of a 1 ng sample of cDNA after 30 amplification cycles with the average amount of cDNA in unamplified samples.

FIG. 2A, comparison of two samples of unamplified cRNA; FIG. 2B, comparison of two 100 ng samples of cDNA after amplification; FIG. 2C, comparison of two 10 ng samples of cDNA after amplification.

FIG. 4A, comparison of two samples of unamplified bladder cDNA, FIG. 4B, comparison of a 100 ng sample of bladder cDNA after amplification with the average amount of cDNA in unamplified samples; FIG. 4C, comparison of a 10 ng sample of bladder cDNA after amplification with the average amount of cDNA in unamplified samples; FIG. 4D, comparison of a 1 ng sample of bladder cDNA after amplification with the average amount of cDNA in unamplified samples.

DETAILED DESCRIPTION OF THE INVENTION

Figure 1A:
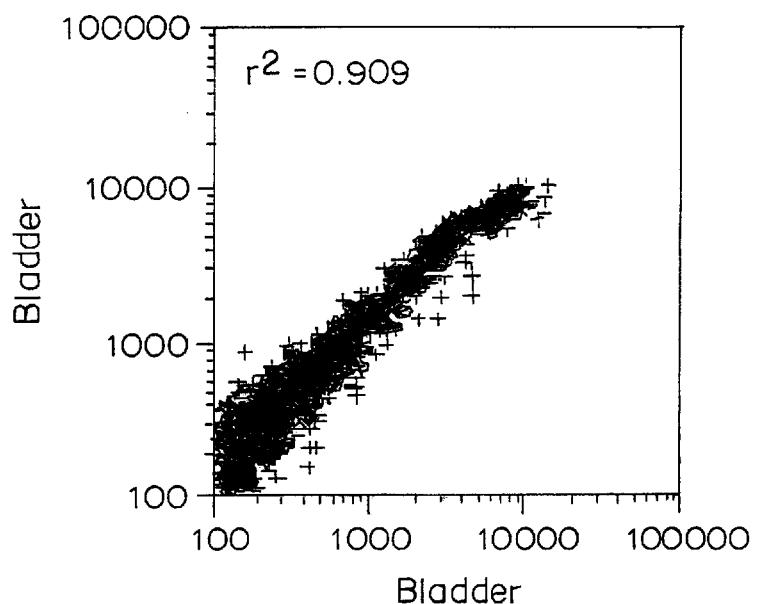
FIGS. 1A–1D are a series of representations depicting the perturbation of the relative amounts of cDNA from various cRNA transcripts from bladder cells after various amplification cycles.
Figure 1B:
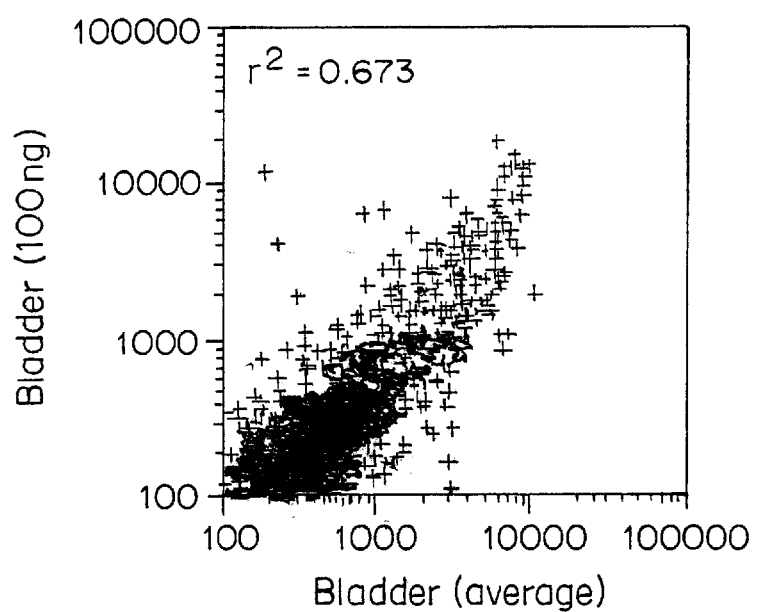
Figure 1C:
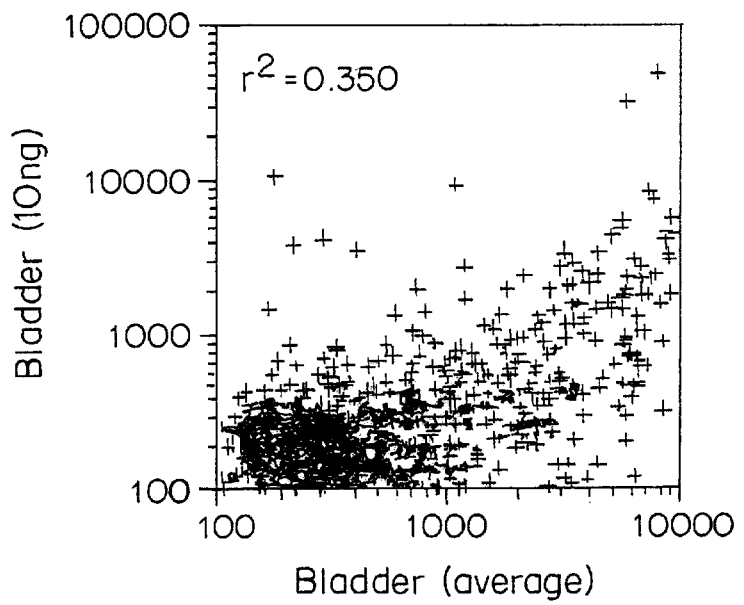
Figure 1D:
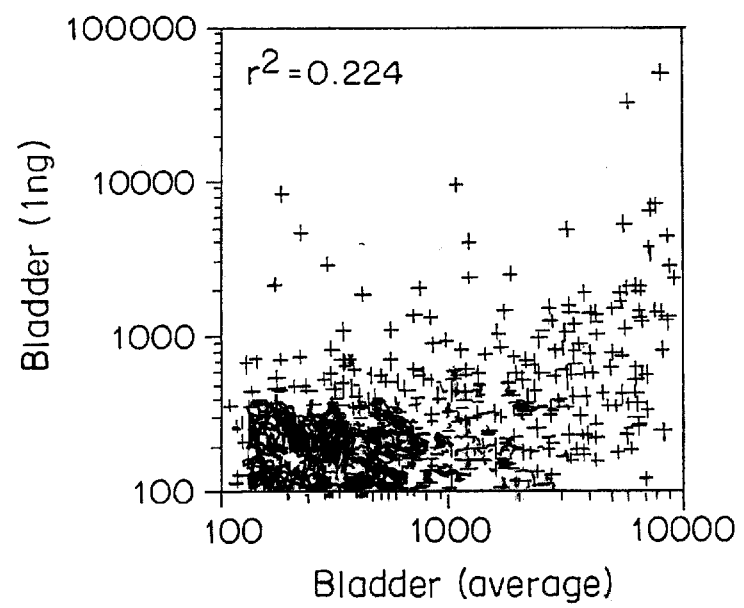

The invention pertains to a means for accurately determining a level or amount of RNA transcripts in a sample, by including a quantitative reference sample during a polymerase chain reaction (PCR) amplification process and correcting for distortion of relative amplified amounts of RNA transcripts. As described herein, Applicants have devised methods of "referenced amplification", which utilize specific labeling of nucleic acid sequences in a reference sample and a test sample, followed by polymerase chain reaction of the combined samples; the methods yield samples in which relative amounts of reference nucleic acids and of test RNA in the amplified samples can be used to determine the transcription levels of the test RNA in the test sample prior to amplification.

In the methods of the invention, a test sample containing RNA is used. In one embodiment, the test sample is obtained from a human individual, who can be an adult, child, or fetus. A test sample from fetal cells or tissue can be obtained by appropriate methods, such as by amniocentesis or chorionic villus sampling. In another embodiment, the test sample can be obtained from a non-human vertebrate, such as a mammal, reptile, amphibian, bird or fish; or from a plant or lower organism (e.g., bacteria). The test sample which contains RNA can be from any source which contains cells comprising RNA, such as a blood sample, sample of amniotic fluid, sample of cerebrospinal fluid, or tissue sample from skin, muscle, placenta, gastrointestinal tract or other organs, or a plant tissue sample or bacterial sample. The RNA in the test sample (the "test RNA") can comprise one or more RNA transcripts of interest. An "RNA transcript of interest," as used herein, is an RNA transcript for which the amount in a non-amplified test sample is sought to be determined. The methods can include not only test samples in which there is a single type of RNA transcript of interest, but also test samples in which there are more than one type of RNA transcript of interest (e.g., in which all types of RNA transcripts are transcripts of interest). The RNA transcript(s) of interest can comprise a known or unknown nucleotide sequence(s). In one embodiment, the test sample comprises a single cell or a small number of cells, such as a tumor cell(s).

The test sample containing test RNA can be processed initially to isolate or partially purify the RNA away from other cellular components, using conventional means (e.g., lysing cells, removing cellular debris, separating the RNA from proteins, lipids or other components present in the mixture) (see, for example, Molecular Cloning, A Laboratory Manual, 2nd ed. (eds. Sambrook et al.) CSH Laboratory Press, Cold Spring Harbor, N.Y. 1989).

In the methods of the invention, a reference sample containing reference nucleic acids is also used. In one embodiment, the reference sample is a sample that is "comparable" to a test sample; that is, the reference sample is from the same source (i.e., from the same organism, and preferably though not necessarily, also of the same tissue or cell type) as the test sample. For example, if the test sample is a sample of human bladder cells, the reference sample can also be a sample of human bladder cells. If the test sample is from an aberrant tissue (e.g., a tumor), the reference sample can be, for example, a sample of the same type of tumor cells, such as from another tumor site or from another individual having the same type of tumor; alternatively, the reference sample can be, for example, a sample of non-aberrant cells from the same tissue (e.g., normal cells surrounding the tumor). More than one type of cell can be used in the reference sample. For example, if the test sample is a tumor, the reference sample can comprise not only tumor cells, but also normal cells. Alternatively, in another embodiment, a normalized nucleic acid library can be used as the reference sample. For example, a pool of nucleic acids (e.g., mRNA) extracted from one or more cell types or tissues (preferably from the same type of organism as the test sample) can be used as a reference sample. In yet another embodiment, a "synthetic" reference sample can be used. A "synthetic" reference sample, as used herein, is a reference sample that is prepared by combining only chosen nucleic acids (e.g., cDNA clones of one or more nucleic acids) into a sample that serves as a reference sample, in contrast with a reference sample as described above that contains a wide spectrum of nucleic acids (e.g., a sample of cells or tissue or a pool of nucleic acids extracted from one or more cell types or tissues). A synthetic reference sample can comprise one type of nucleic acid (e.g., nucleic acids comprising a single gene), or more than one type of nucleic acid (e.g., nucleic acids comprising more than one gene), and can also include other components if desired.

The reference sample comprises a known amount of nucleic acids (e.g., gene, cDNA, RNA), referred to herein as the "reference nucleic acids". If desired, the reference sample can be processed in a similar manner as the test sample, to isolate or partially purify the reference nucleic acids away from other cellular components, using conventional means as described above. In a preferred embodiment, the reference sample is the total RNA from a comparable sample.

The reference nucleic acid in the reference sample and test RNA in the test sample are labeled at the 5' end with an oligonucleotide that allows differentiation of the reference nucleic acids from the test RNA. The oligonucleotide is a first strand 5' cDNA primer sequence containing a unique and different "specificity determining box" for the reference nucleic acid and for the test RNA. The specificity determining box is a unique, short (approximately 4–8 nucleotides, preferably 5 nucleotides) nucleotide sequence. The specificity determining box for the reference sample is the "reference specificity determining box", and the specificity determining box for the test sample is the "test specificity determining box". In one embodiment, the base composition of the reference specificity determining box is the same as the base composition of the test specificity determining box, and the bases are arranged differently for each box. In other embodiments, the nucleotide composition of the specificity determining boxes can be completely random, provided that the reference specificity determining box differs from the test specificity determining box.

The first strand 5' cDNA primer contains a partial RNA polymerase promoter sequence. A "partial" sequence is an amount of the promoter that is not sufficient to allow polymerization with the polymerase. The RNA polymerase promoter sequence can be from various enzymes used for polymerization, such as SP6, T3, or T7 RNA polymerase. The first strand 5' cDNA primer also contains a polyT sequence having approximately 15–50 T, preferably approximately 20–30 T, and even more preferably 24 T. The specificity determining box (either reference or test) is between the partial RNA polymerase promoter sequence and the polyT sequence. The first strand 5' cDNA primer consists essentially of these three components (partial RNA polymerase promoter sequence, specificity determining box, and polyT sequence). If desired, other components can also be included in the first strand 5' cDNA primer (e.g., other nucleic acids), provided that the 5' cDNA primer also includes these three components in the indicated order. The first strand 5' cDNA primers are identical except for the specificity determining box. In one embodiment, the first strand 5' cDNA primer with a reference specificity determining box contains a partial T7 RNA polymerase promoter, a specificity determining box, and a 24T polyT sequence (e.g., TCACTATAGGGAGGCGGATCGC(T)24VN (SEQ ID NO:1), or

CTCACTATAGGGAGGCGGCAGCT(T)24VN (SEQ ID NO:2)).

The reference nucleic acid in the reference sample and test RNA in the test sample are also labeled at the 3' end with a common 3' first strand cDNA primer sequence (i.e., the same 3' first strand cDNA primer sequence is used for the reference nucleic acid and for the test RNA). The common 3' first strand cDNA primer can be approximately 10–40 nucleotides long, preferably approximately 20–30 nucleotides long, and even more preferably approximately 23 nucleotides long (e.g., the primer attached using the SMART™ kit (CLONTECH Laboratories, Inc., Palo Alto, Calif.), having sequence AAGCAGTGGTAACGCA-GAGTGGG (SEQ ID NO:3)). The 3' first strand cDNA primer can be any type of unique primer that can be used to amplify the nucleic acids using the polymerase chain reaction, and can be attached to the reference nucleic acids and to the test RNA using standard methods (e.g., ligation, hybridization, strand switching).

The reference sample and the test sample are combined to form a sample mixture. The sample mixture is then subjected to amplification conditions for polymerase chain reaction (PCR). See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202; the entire teachings of which are incorporated herein by reference. Amplification conditions include buffers, reagents and other conditions (e.g., temperature, automated cycling conditions) that are sufficient to allow amplification of the reference nucleic acid and the test RNA by polymerase chain reaction. Amplification conditions include the addition of dNTPS, buffers, enzymes, and universal primers. "Universal primers" are nucleic acid primers which specifically bind to the 5' and 3' first strand cDNA primer sequences, with which the reference nucleic acid and test RNA were labeled; for example, the universal primers can be nucleic acid primers which specifically bind to the partial RNA polymerase promoter sequence on the 5' first strand cDNA primer, and which specifically bind to the common 3' first strand cDNA primer sequence. In one embodiment, the universal primers are the Universal Forward primer, CGACTCACTATAGG-GAGGCGG (SEQ ID NO:4) and the Universal Reverse primer, AAGCAGTGGTAACAACGCACACT (SEQ ID NO:5). Representative amplification conditions include cycling parameters of 10 minutes at 95° C., followed by cycles of 30 seconds at approximately 95° C., 30 seconds at approximately 60° C., 6 minutes at approximately 72° C. The number of cycles varies, depending on the RNA abundance, and can be determined empirically. Generally, approximately 5 to 30 cycles are used. Amplification of the reference nucleic acid and of the test RNA results from incubation under amplification conditions; the resultant amplified sample mixture thus comprises amplified amounts of both the reference nucleic acid and cDNA of the test RNA in the sample mixture.

Following amplification, the amplified sample mixture is divided in two parts (a first divided sample mixture, in which the amplified amount of the reference nucleic acid will be assessed, and a second divided sample mixture, in which the amplified amount of cDNA of the test RNA will be assessed). The divided sample mixtures are subjected to additional amplification conditions (referred to herein as "continued amplification conditions") which are sufficient for continued amplification of the nucleic acids in the sample mixture, such as by PCR or by linear extension (similar to PCR, except using a single primer). See *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202, as referenced above. In a preferred embodiment, linear extension is used. Continued amplification conditions include buffers, reagents and other conditions (e.g., temperature, automated cycling conditions) that are sufficient to allow further amplification of the amplified reference nucleic acid and of the amplified test RNA. Continued amplification conditions include: addition of dNTPS, buffers, enzymes, and continued amplification primers (e.g., linear extension primers if linear extension is used). The continued amplification primers include the complete RNA polymerase promoter, for which the partial RNA polymerase promoter sequence was used in the first strand 5' cDNA primer (i.e., if a partial T7 RNA polymerase promoter was used in the first strand 5' cDNA primer, the complete T7 RNA polymerase promoter is used in the continued amplification primer). The continued amplification primers also specifically bind to the 5-nucleotide specificity determining box for either the reference sample or the test sample (i.e., the reference specificity determining box or the test specificity determining box). In one embodiment, the continued amplification primers include the primer, GGCCAGT-GAATTGTAATACGACTCACTATAGGGAG-GCGGATCGT (SEQ ID NO: 6) for one specificity determining box (the one for which SEQ ID NO:1 was used as the first strand 5' cDNA primer), and the primer, GGCCAGT-GAATTGTAATACGACTCACTATAGGGAG GCGGCAGCTT, (SEQ ID NO:7) for the second specificity determining box (the one for which SEQ ID NO:2 was used as the first strand 5' cDNA primer). Representative continued amplification conditions include cycling parameters of 10 minutes at 95° C., followed by 5 cycles of 30 seconds at approximately 95° C., 30 seconds at approximately 68° C., 6 minutes at approximately 72° C. Continued amplification of the divided sample mixtures results in the presence of nucleic acids which comprise the amplified reference nucleic acid (in the first divided sample mixture) or amplified cDNA of the test RNA (in the second divided sample mixture).

Because the complete RNA polymerase promoter is present in the resultant nucleic acids, in vitro transcription (IVT) can be performed to generate cDNA or cRNA from the amplified reference nucleic acids in the first divided sample mixture, and amplified cDNA of the test RNA in the second divided sample mixture (see, e.g., M. Mahadevaparra and J. A. Warrington, *Nat. Biotechnol.* 17(11):1134–6 (1999)). The cDNA or cRNA can be labeled to facilitate detection. Representative labels include incorporation of radionuclides or fluorescently-labeled nucleotides into the cDNA or cRNA, or biotin labeling of the cDNA or cRNA. In a preferred embodiment, the cDNA or cRNA is labeled with biotin. If desired, a few rounds of PCR or linear extension can be used to incorporate labeled nucleotides into cDNA for analysis.

The amount of amplified reference nucleic acid and the amount of amplified cDNA of the test RNA, or the correlating labeled cRNAs, can be used to assess the amount of test RNA that was present in the test sample before amplification was performed. As described in the Exemplification below, nucleic acids behave similarly or identically in separately amplified samples (using the same amplification conditions); that is, the amplification characteristics, such as degree of amplification, are the same for separately amplified samples. It is therefore expected that the reference nucleic acid and the test RNA will also behave similarly in terms of amplification characteristics, including the degree of amplification, when mixed and thereby exposed to the same amplification conditions. Thus, the amount of test RNA in the amplified sample mixture is expected to be amplified to the same degree as the amount of the reference nucleic acid in the amplified sample mixture. The amplified amount of the test RNA therefore correlates directly with the amount of amplified reference nucleic acid in the amplified sample mixture; and similarly, the initial test sample correlates directly with the amount of the reference nucleic acid in the initial reference sample before amplification. For example, the amount or expression level of the test RNA in the initial test sample (i.e., before amplification) can be determined as a ratio of the amount of amplified test RNA over the amount of the amplified reference nucleic acid, multiplied by the amount of the reference nucleic acid in the initial reference sample (prior to amplification). Alternatively, the amount or expression level of the test RNA can be determined as a ratio of the amount of cDNA or cRNA prepared from the amplified test RNA, over the amount of cDNA or cRNA prepared from the amplified reference nucleic acid, multiplied by the amount of the reference nucleic acid in the reference sample prior to amplification. If desired, the amount of a single RNA transcript of interest can also be determined using similar means (e.g., the amount or expression level of the RNA transcript of interest can be determined as a ratio of the amount of cDNA or cRNA of the RNA transcript of interest in the amplified test RNA, over the amount of cDNA or cRNA prepared from the amplified reference nucleic acid, multiplied by the amount of the reference nucleic acid in the reference sample prior to amplification).

In one embodiment, the amount or expression of the test RNA (or the RNA transcript of interest) can be determined by microarray analysis, such as described in M. Mahadevaparra and J. A. Warrington, *Nat. Biotechnol.* 17(11):1134–6 (1999), the entire teachings of which are incorporated by reference herein.

The methods of the invention can be used for accurate quantification of RNA transcripts of interest in small samples, including single-cell samples. With accurate measurement of RNA transcripts of interest, it is now possible to identify transcripts that are involved in clonal events or single cell differentiation without risk of mistakenly interpreting as important an RNA transcript which has distorted amplification during PCR, relative to other RNA transcripts. Furthermore, methods such as microarray technology can now be employed for analysis of transcripts from small samples.

The invention is further illustrated by the following Exemplification, which is not intended to be limiting. The teachings of all references cited herein are incorporated by reference in their entirety.

EXEMPLIFICATION

Referenced Amplification of RNA
Materials and Methods
Purified total cellular RNA (bladder or brain) was purchased from Invitrogen (Carlsbad, Calif.).
cDNA Generation and Labeling of Reference Samples and Test RNA
Total RNA in samples were processed essentially according to the SMART™ kit protocol (CLONTECH Laboratories, Inc., Palo Alto, Calif.), except that the CDS primer was replaced with either polyT-1

(CTCACTATAGGGAGGCGGATCGC(T)24VN) (SEQ ID NO:1) or polyT-2

(CTCACTATAGGGAGGCGGCAGCT(T)24VN) (SEQ ID NO:2) at the recommended concentration.

PCR Using Universal Primers
PCR was carried out using the Universal Forward primer (CGACTCACTATAGGGAGGCGG) (SEQ ID NO:4) and the Universal Reverse primer (AAGCAGTGGTAACAACGCACACT) (SEQ ID NO:5). The appropriate cDNA reactions described above were pooled and co-amplified with the Universal primer set in a total volume of 500 µl (10× PCR buffer (Perkin Elmer), 12.5 Utaq gold, 200 mM dNTPs, 500 nM each primer, final concentration) for the appropriate number of cycles. Cycling parameters were as follows: 10 minutes at 95° C., followed by cycles of 30 seconds at 95° C., 30 seconds at 60° C., 6 minutes at 72° C.; and a final extension step of 10 minutes at 72° C. Nucleotide and primer removal was accomplished using the Qiaquick PCR spin column according to manufacturer's recommendations (Qiagen, Valencia, Calif.). The PCR product was then eluted in 50 µl warm distilled water.
Linear Extension
For each linear extension, 20 µl of the appropriate sample was combined with primer T7-1 (GGCCAGTGAATGGTAATACGACTCACTATAGGGA GGCGGATCGCT, SEQ ID NO:6) (following use of SEQ ID NO:1), or primer T7-2 (GGCCAGTGAATTGTAATACGACTCACTATAGGGA GGCGGCAGCTT, SEQ ID NO:7) (following use of SEQ ID NO:2). Each extension was performed in a 100 µl volume (10×PCR buffer (Perkin Elmer), 2.5 U taq gold, dNTPs). Cycling parameters were as follows: 10 minutes at 95° C., followed by 5 cycles of 30 seconds at 95° C., 30 seconds at 68° C., 6 minutes at 72° C. and a final extension step of 10 minutes at 72° C. These products were then run on an agarose gel to verify that amplification had taken place. Further removal of unincorporated nucleotides and primer was performed as described by M. Mahadevaparra and J.A. Warrington, *Nat. Biotechnol.* 17(11):1134–6 (1999).

cRNA Labeling and Generation

Biotin-labeled cRNA was generated as described by M. Mahadevaparra and J. A. Warrington, *Nat. Biotechnol.* 17(11):1134–6 (1999). All cRNA concentrations were measured using a standard spectrophotomer.

cRNA Generation for Unamplified Samples

For each sample, 20 μg of total RNA was taken and processed as described by M. Mahadevaparra and J. A. Warrington, *Nat. Biotechnol.* 17(11):1134–6 (1999).

Hybridization of Sample to Microarrays and Analysis

Hybridization of gene chips (Affymetrix HD GeneChip® array) was done according to manufacturer's protocol (Affymetrix, Santa Clara, Calif.). All data were filtered using a cut-off of 100 of the average difference value. Inferred values are always based on calls above 100 in both amplified samples and reference samples, and a call of at least 100 in the unamplified reference samples.

Results

In order to assess the effects of amplification of RNA on the relative representation of individual mRNAs in a sample, unamplified cRNA generated from 10 μg of total bladder RNA in two separate samples was compared with the amplified cRNA for sets of smaller samples (100 ng, 10 ng or 1 ng) amplified for different numbers of cycles (20 cycles, 25 cycles, or 30 cycles, respectively). The comparison revealed that amplification over- or under-amplified the vast majority of genes. In fact, after 30 cycles of PCR, very little correlation remained between the amount of unamplified cRNA and amplified cRNA (FIGS. 1A–1D). Thus, exponential amplification alone cannot be used to assess expression levels.

Figure 2A:
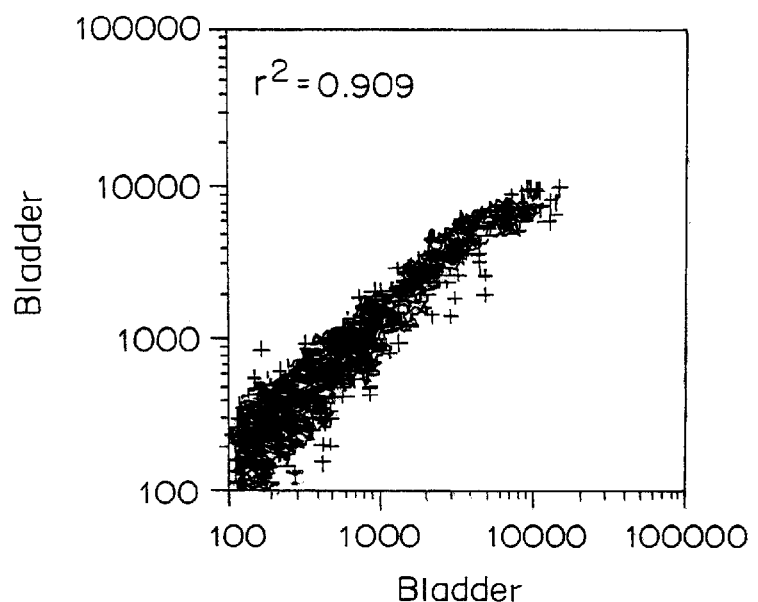
FIGS. 2A–2C are a series of representations depicting the retention of the relative amounts of cDNA from cRNA transcripts after amplification with initially varying amounts of cRNA transcripts from bladder cells.
Figure 2B:
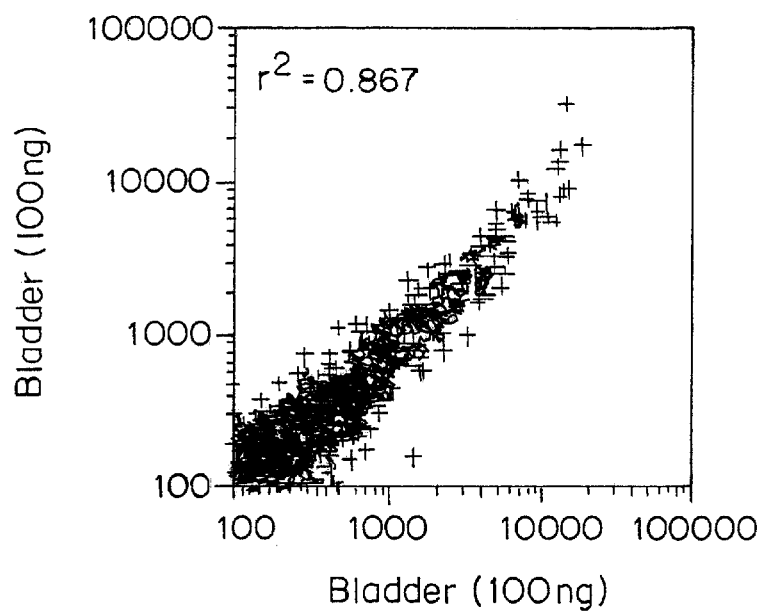
Figure 2C:
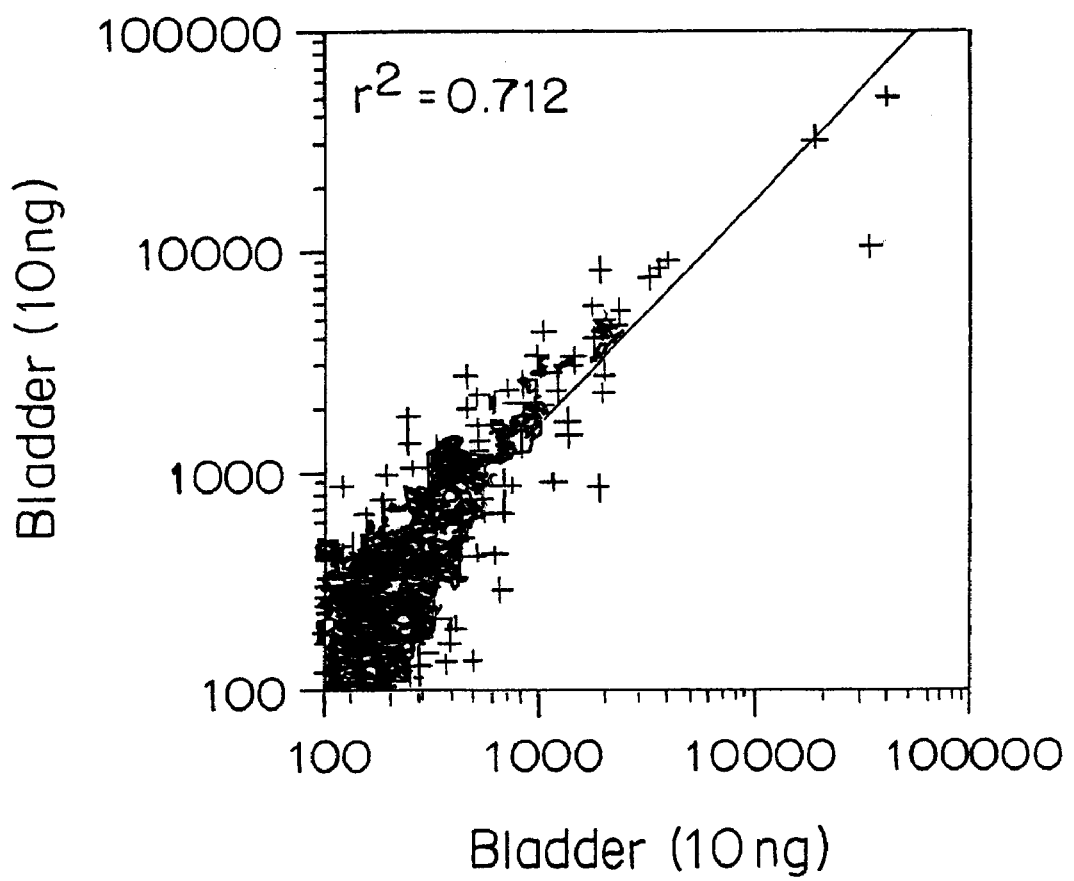

In order to assess whether relative abundance after exponential amplification was gene specific, the amplification of 100 ng and 10 ng of total bladder RNA was performed and the relative levels of the RNA were compared to the levels in an unamplified cRNA sample. As can be seen in FIGS. 2A (unamplified), 2B (100 ng, amplified) and 2C (10 ng, amplified), identical genes behave similarly or identically in terms of amplification characteristics when comparing two independently amplified samples, regardless of the initial amount of total RNA. The variability increased with higher cycle number and with lower hybridization intensity. However, because amplified samples differ from each other more than unamplified samples, it is presumed that tube to tube variability plays a role as well.

Figure 3:
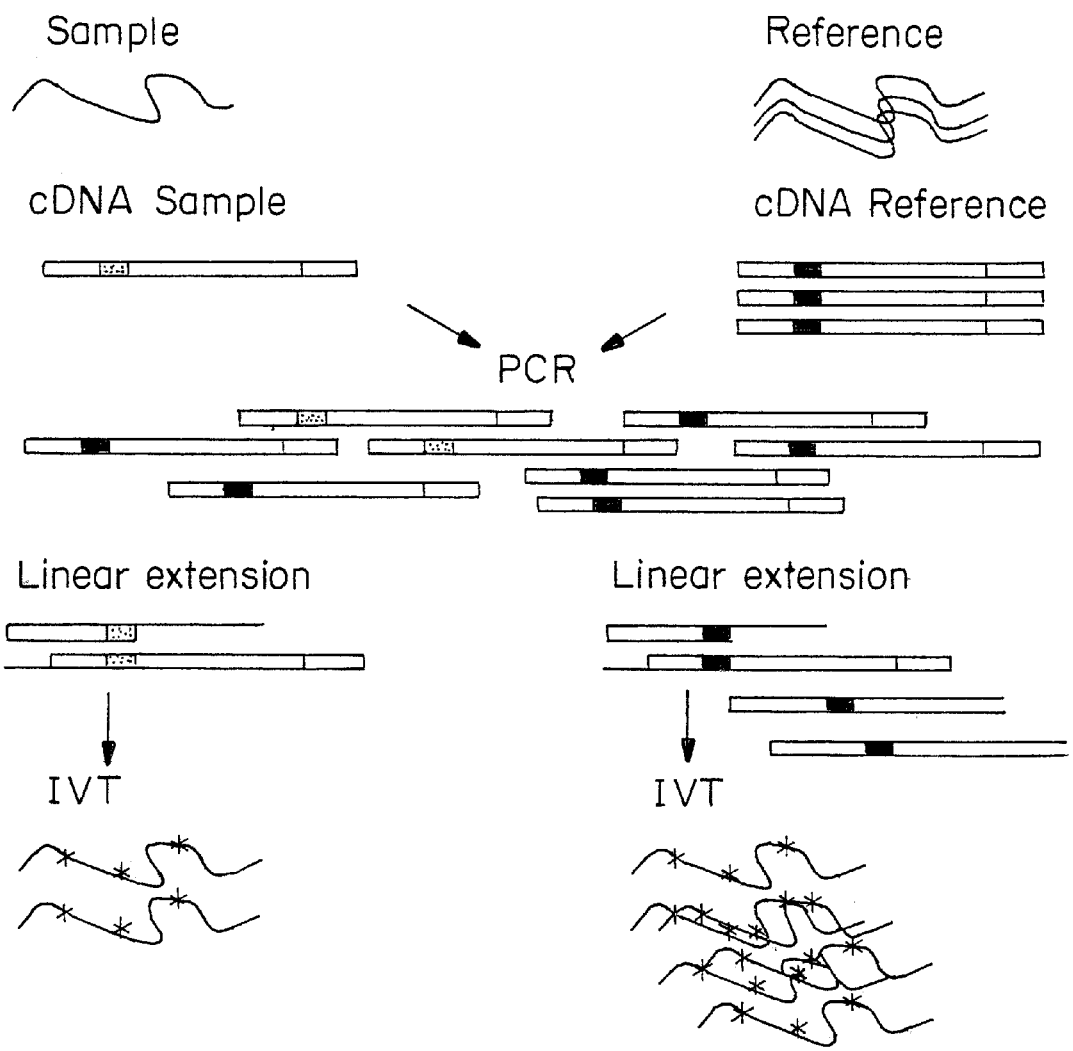
FIG. 3 is a flow diagram depicting the method used to correct for perturbation of relative amounts of cDNA after amplification.
Figure 4A:
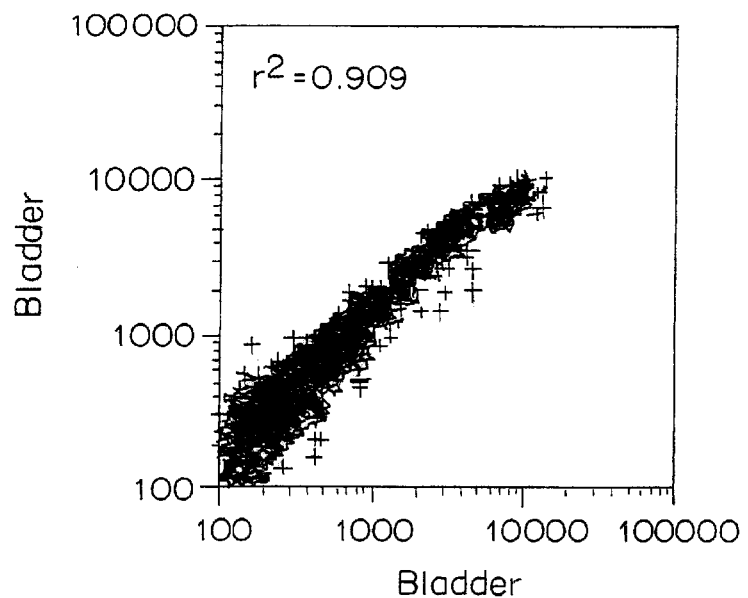
FIGS. 4A–4D are a series of representations depicting the relative amounts of cDNA from cRNA transcripts after referenced amplification which corrected for distortion of relative amounts of transcripts that can occur during amplification.
Figure 4B:
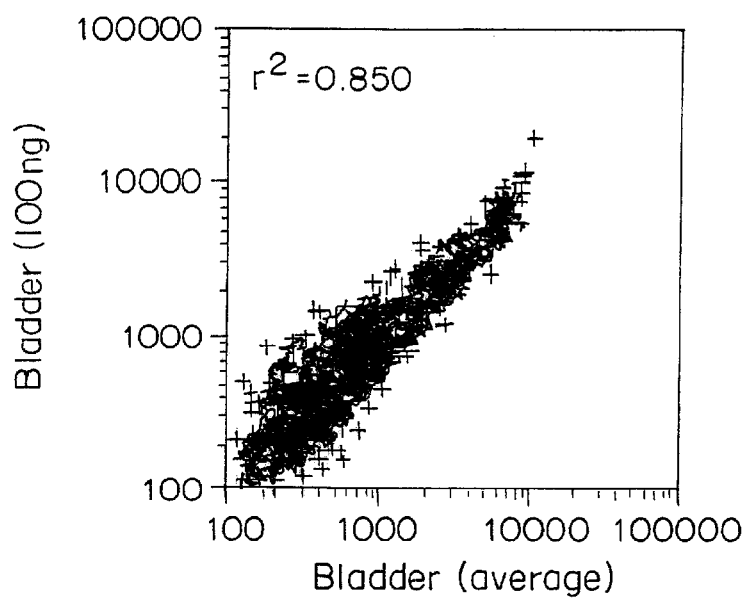
Figure 4C:
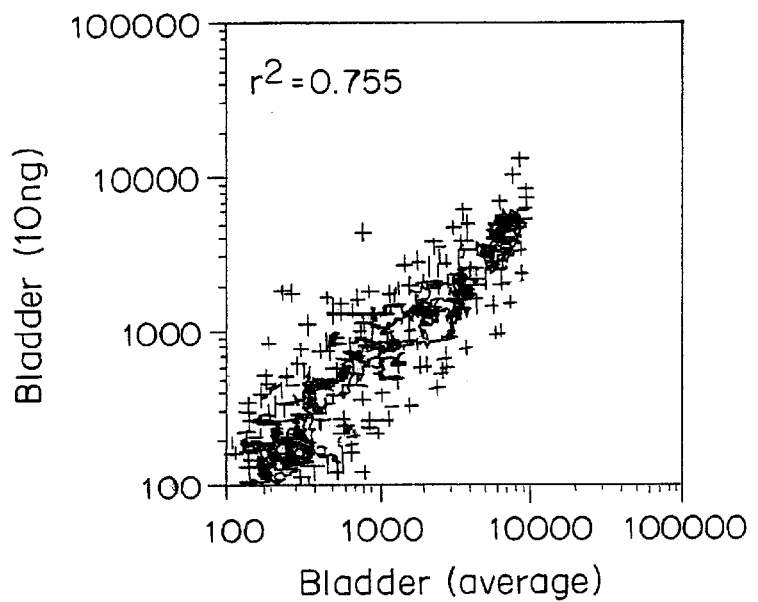
Figure 4D:
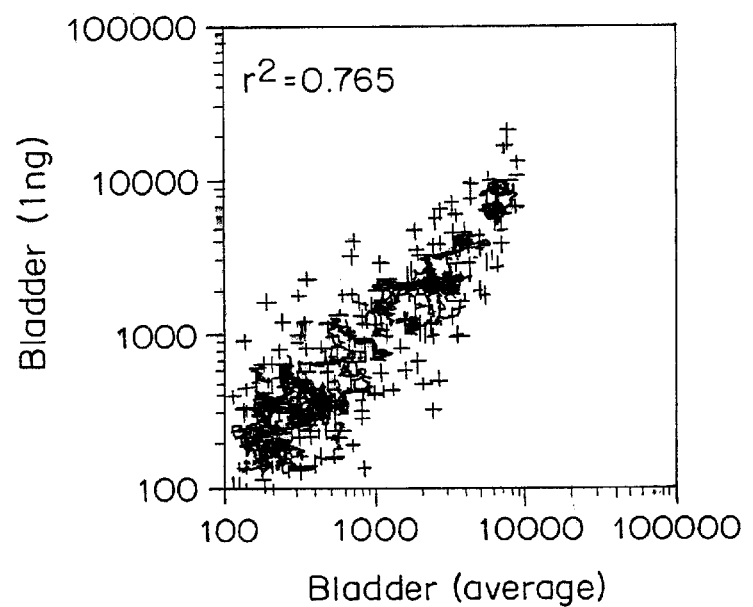

Given the sequence-specific nature of the over- or under-amplification of particular sequences, an amplification method was designed to correct for over- or under-amplification, utilizing a labeled reference population with known gene expression levels, that was co-amplified with a test sample. In order to distinguish and separate the reference sample from the test sample after co-amplification, they were each labeled with a unique 5-base sequence. This 5-base specificity determining box was designed in between the polyT region used for first strand synthesis, and a common sequence which was used for the common amplification of experimental and reference sample. After first strand synthesis, which included the addition of a unique primer sequence to the 3' part of the first strand cDNA (e.g., using the Invitrogen SMART kit system), equal amounts of reference and test sample were combined and amplified using common primers. In order to assay the expression levels of the reference sample or the test sample separately, a linear extension reaction was performed using a primer containing a fully functional T7 RNA polymerase promoter and ending in a base sequence complementary to either one of the specificity determining box sequences. Finally, labeled cRNA was generated from the experimental and reference samples separately by in vitro transcription (IVT), and both samples were hybridized to a microarray for analysis. A flow diagram of the procedure is shown in FIG. 3.

In order to infer the expression level of a given gene in the test sample before amplification, the ratio of the value of the amplified test sample and reference sample was multiplied by the level of the gene in the unamplified reference sample. To determine the validity of this method, samples containing 1 ng, 10 ng, and 100 ng quantities of total bladder RNA were used. A reference sample was constructed by mixing equal quantities of total bladder RNA and total brain RNA. After reference amplification, all samples were hybridized to Affymetrix HD GeneChip® arrays (Affymetrix) and inferred levels of expressed genes were calculated. Results, shown in FIGS. 4A–4D, demonstrate correction for skewing caused by PCR.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of determining the amount of test RNA in a test sample, comprising:
   a. admixing:
      i) a reference sample, wherein the reference sample comprises a known amount of a reference nucleic acid, wherein the reference nucleic acid comprises a first strand 3' cDNA primer sequence and a first strand 5' cDNA primer sequence comprising a reference specificity determining box; and
      ii) a test sample comprising an amount of test RNA, wherein the test RNA comprises the first strand 3' cDNA primer sequence and a first strand 5' cDNA primer sequence comprising a test specificity determining box, thereby providing a sample mixture;
   b. subjecting the sample mixture to amplification conditions for polymerase chain reaction, thereby producing an amplified sample mixture;
   c. dividing the amplified sample mixture into a first divided sample mixture and a second divided sample mixture;
   d. subjecting the first divided sample mixture to continued amplification conditions, wherein the continued amplification conditions comprise using continued amplification primers that specifically bind to the reference specificity determining box, thereby producing nucleic acids comprising amplified reference nucleic acid; and subjecting the second divided sample mixture to continued amplification conditions, wherein the continued amplification conditions comprise using continued amplification primers that specifically bind to the test specificity determining box, thereby producing nucleic acids comprising amplified cDNA of the test RNA; and
   e. determining the amount of test RNA in the test sample, wherein the amount of the test RNA in the test sample correlates with a ratio of the amount of amplified cDNA of the test RNA over the amount of the amplified reference nucleic acid, multiplied by the known amount of the reference nucleic acid in the reference sample.

2. The method of claim 1, wherein the first strand 5' cDNA primer sequence comprising a reference specificity determining box, comprises a partial RNA polymerase promoter sequence, a polyT sequence, and a reference specificity determining box between the partial RNA polymerase promoter sequence and the polyT sequence.

3. The method of claim 2, wherein the partial RNA polymerase promoter sequence is from an RNA polymerase promoter selected from the group consisting of: SP6, T3 or T7 RNA polymerase promoter.

4. The method of claim 2, wherein the polyT sequence contains approximately 15–50 T.

5. The method of claim 4, wherein the polyT sequence contains approximately 24 T.

6. The method of claim 3, wherein the first strand 5' cDNA primer sequence comprising a reference specificity determining box comprises CTCACTATAGGGAGGCGGATCGC(T)24VN (SEQ ID NO:1).

7. The method of claim 1, wherein the first strand 5' cDNA primer sequence comprising a test specificity determining box, comprises a partial RNA polymerase promoter sequence, a polyT sequence, and a test specificity determining box between the partial RNA polymerase promoter sequence and the polyT sequence.

8. The method of claim 7, wherein the partial RNA polymerase promoter sequence is from an RNA polymerase promoter selected from the group consisting of: SP6, T3 or T7 RNA polymerase promoter.

9. The method of claim 7, wherein the polyT sequence contains approximately 15–50 T.

10. The method of claim 9, wherein the polyT sequence contains approximately 24 T.

11. The method of claim 7, wherein the first strand 5' cDNA primer sequence comprising a test specificity determining box comprises CTCACTATAGGGAGGCGGCAGCT(T)24VN (SEQ ID NO:2).

12. The method of claim 1, wherein the amplification conditions for polymerase chain reaction comprise using universal primers which specifically bind to the 5' first strand cDNA primer sequences and to the 3' first strand cDNA primer sequences of both the reference nucleic acid and the test RNA.

13. The method of claim 12, wherein the universal primers comprise CGACTCACTATAGGGAGGCGG (SEQ ID NO:4) and AAGCAGTGGTAACAACGCACACT (SEQ ID NO:5).

14. The method of claim 1, wherein the amplification conditions for polymerase chain reaction comprise cycling parameters of 10 minutes at 95° C., followed by approximately 5 to 30 cycles of 30 seconds at approximately 95° C., 30 seconds at approximately 60° C., and 6 minutes at approximately 72° C.

15. The method of claim 6, wherein the continued amplification primers that specifically bind to the reference specificity determining box comprise GGCCAGTGAATTG-TAATACGACTCACTATAGGGAGGCGGATCGT (SEQ ID NO: 6).

16. The method of claim 11, wherein the continued amplification primers that specifically bind to the test specificity determining box comprise GGCCAGTGAATTG-TAATACGACTCACTATAGGGAG GCGGCAGCTT, (SEQ ID NO:7).

17. The method of claim 1, wherein the continued amplification conditions comprise cycling parameters of 10 minutes at 95° C., followed by 5 cycles of 30 seconds at approximately 95° C., 30 seconds at approximately 68° C., and 6 minutes at approximately 72° C.

18. The method of claim 1, wherein the reference specificity determining box and the test specificity determining box have the same base composition.

19. The method of claim 1, wherein the amount of amplified cDNA of the test RNA, the amount of the amplified reference nucleic acid, and the known amount of the reference nucleic acid in the reference sample are assessed using microarray analysis.

20. A method of determining the amount of test RNA in a test sample, comprising:
  a) admixing:
    i) a reference sample, wherein the reference sample comprises a known amount of a reference nucleic acid, wherein the reference nucleic acid comprises a first strand 3' cDNA primer sequence and a first strand 5' cDNA primer sequence comprising a reference specificity determining box; and
    ii) a test sample comprising an amount of test RNA, wherein the test RNA comprises the first strand 3' cDNA primer sequence and a first strand 5' cDNA primer sequence comprising a test specificity determining box, thereby providing a sample mixture;
  b) subjecting the sample mixture to amplification conditions for polymerase chain reaction, thereby producing an amplified sample mixture;
  c) dividing the amplified sample mixture into a first divided sample mixture and a second divided sample mixture;
  d) subjecting the first divided sample mixture to linear extension conditions, wherein the linear extension conditions comprise using linear extension primers that specifically bind to the reference specificity determining box, thereby producing nucleic acids comprising amplified reference nucleic acid; and subjecting the second divided sample mixture to linear extension conditions, wherein the linear extension conditions comprise using linear extension primers that specifically bind to the test specificity determining box, thereby producing nucleic acids comprising amplified cDNA of the test RNA; and
  e) determining the amount of test RNA in the test sample, wherein the amount of the test RNA in the test sample correlates with a ratio of the amount of amplified cDNA of the test RNA over the amount of the amplified reference nucleic acid, multiplied by the known amount of the reference nucleic acid in the reference sample.

21. A method of determining the amount of an RNA transcript of interest in a test sample, comprising:
  a) admixing:
    i) a reference sample, wherein the reference sample comprises a known amount of a reference nucleic acid, wherein the reference nucleic acid comprises a first strand 3' cDNA primer sequence and a first strand 5' cDNA primer sequence comprising a reference specificity determining box; and
    ii) a test sample comprising an amount of test RNA, wherein the test RNA comprises the first strand 3' cDNA primer sequence and a first strand 5' cDNA primer sequence comprising a test specificity determining box, thereby providing a sample mixture;
  b) subjecting the sample mixture to amplification conditions for polymerase chain reaction, thereby producing an amplified sample mixture;
  c) dividing the amplified sample mixture into a first divided sample mixture and a second divided sample mixture;
  d) subjecting the first divided sample mixture to continued amplification conditions, wherein the continued amplification conditions comprise using continued amplification primers that specifically bind to the reference specificity determining box, thereby producing nucleic acids comprising amplified reference nucleic acid; and subjecting the second divided sample mixture to continued amplification conditions, wherein the continued amplification conditions comprise using continued amplification primers that specifically bind to the test specificity determining box, thereby producing nucleic acids comprising amplified cDNA of the test RNA containing amplified RNA transcript of interest; and
  e) determining the amount of the RNA transcript of interest in the test sample, wherein the amount of the RNA transcript of interest in the test sample correlates with a ratio of the amount of cDNA of the amplified RNA transcript of interest in the amplified cDNA of the test RNA, over the amount of the amplified reference nucleic acid, multiplied by the known amount of the reference nucleic acid in the reference sample.

* * * * *

UNITED STATES PATENT AND TRADEMARK OFFICE
CERTIFICATE OF CORRECTION

PATENT NO. : 6,602,665 B2  Page 1 of 1
DATED : August 5, 2003
INVENTOR(S) : David de Graaf and Eric S. Lander It is certified that error appears in the above-identified patent and that said Letters Patent is hereby corrected as shown below:

<u>Column 13,</u>
Line 47, "amplilied" should be -- amplified --.

Signed and Sealed this

Twenty-eighth Day of October, 2003

JAMES E. ROGAN
*Director of the United States Patent and Trademark Office*